(12) United States Patent
Grawe et al.

(10) Patent No.: US 8,324,412 B2
(45) Date of Patent: Dec. 4, 2012

(54) METHOD FOR PREPARING 4-[17β-METHOXY-17α-METHOXYMETHYL-3-OXOESTRA-4,9-DIEN-11β-YL]BENZALDEHYDE (E)-OXIME (ASOPRISNIL)

(75) Inventors: Detlef Grawe, Kleinromstedt (DE); Sabine Gliesing, Jena (DE); Hagen Gerecke, Jena (DE); Peter Hoesel, Jena (DE); Uwe Mueller, Jena (DE); Thomas Michel, Leipzig (DE); Robert Eilers, Jena (DE); Uwe Knabe, Trockenborn (DE); Bernd Erhart, Kahla (DE); Michael Mosebach, Berlin (DE); David Voigtlaender, Bad Vilbel (DE); Ulf Tilstam, Hoegaarden (BE); Jürgen Jacke, Unna (DE); Klaus Bahl, Herne (DE); Ulf Bohlmann, Köln (DE); Dieter Wehmeier, Bergkamen (DE); Michael Sander, Frechen (DE)

(73) Assignee: Bayer Pharma AG, Berlin (DE)

( * ) Notice: Subject to any disclaimer, the term of this patent is extended or adjusted under 35 U.S.C. 154(b) by 0 days.

(21) Appl. No.: 12/987,850

(22) Filed: Jan. 10, 2011

(65) Prior Publication Data

US 2011/0257142 A1    Oct. 20, 2011

Related U.S. Application Data

(63) Continuation of application No. 11/785,421, filed on Apr. 17, 2007, now abandoned.

(60) Provisional application No. 60/792,643, filed on Apr. 18, 2006.

(51) Int. Cl.
*C07J 1/00* (2006.01)
(52) U.S. Cl. ........................................ 552/648
(58) Field of Classification Search .................. 552/648
See application file for complete search history.

(56) References Cited

U.S. PATENT DOCUMENTS

| | | | |
|---|---|---|---|
| 2004/0006241 A1 | 1/2004 | Grawe et al. | |
| 2004/0063172 A1 | 4/2004 | Schubert et al. | |

FOREIGN PATENT DOCUMENTS

| | | |
|---|---|---|
| DE | 100 56 675 A1 | 5/2002 |
| DE | 103 11 092 A1 | 10/2004 |
| DE | 10 2004 021 060 A1 | 11/2005 |
| FR | 5 183 M | 6/1967 |
| WO | WO 01/90137 A2 | 11/2001 |

OTHER PUBLICATIONS

Tilstam Ulf, "Use of trifluoroacetic acid and cyclohexanone to prepare steroidal 17-ketones by Oppenauer," Publication Date: Oct. 7, 2004; English Abstract of DE10311092.

Kloss Sibylle, "Pharmaceutical substance steroid production installation cross contamination reduction procedure uses special investigation techniques," Publication Date: Nov. 24, 2005; English Abstact of DE 102004021060.

Brown, J. J. et al., "A Novel Isomerization of Steroidal $\Delta^{4,9(10)}$-3-Ketones," Steroids, Organic Chemical Research Section, Lederle Laboratories, A Division of American Chemical Cyanamid Co., Jan. 1963, vol. 1, pp. 113-116.

Brown, J. J. et al., "The Preparation of Steroidal $\Delta^{5(10),9(11)}$-3-Ketones.[1]," Steriods,Organic Chemical Research Section, Lederle Laboratories, A Division of American Cyanamid Company, May 30, 1966, vol. 8, No. 1.

Gebhard, R et al., "11,21-Bisphenyl-19-norpregnane derivatives are selective antiglucocorticoids," Bioorganic & Medicinal Chemistry Letters, 1997, vol. 7, No. 17, pp. 2229-2234.

Liu, A et al., "Synthesis of High Affinity Fluorine-Substituted Ligands for the Androgen Receptor. Potential Agents for Imaging Prostatic Cancer by Positron Emission Tomography," J. Med. Chem., 1992, vol. 35, pp. 2113-2129.

Hubner, M et al., "Synthase potentieller Metaboliten der STS 557 (Dienogest)1" Pharmazie, 1984, vol. 39, pp. 496-497.

Roussel-Uclaf, "Nouveau medicament notamment pour le traitement des troubles dus a une insuffisance de secretion du corps jaune," Brevet Special de Medicament, Mar. 4, 1966.

B. Mezenbach et al., "Synthesis of Potential Metabolites of STS 557 (Diengest)", Pharmazie, vol. 39, No. 7 (1984) pp. 496-497.

*Primary Examiner* — Barbara P Badio
(74) *Attorney, Agent, or Firm* — Millen, White, Zelano & Branigan, P.C.

(57) ABSTRACT

The present invention relates to a method for the reliable and reproducible preparation of 4-[17β-methoxy-17α-methoxymethyl-3-oxoestra-4,9-dien-11β-yl]benzaldehyde (E)-oxime (asoprisnil) on the pilot and manufacturing scale. Asoprisnil, which is prepared by this method, is distinguished by a very good physical stability and is therefore particularly suitable for the manufacture of solid pharmaceutical forms (tablets, coated tablets, etc.).

18 Claims, 3 Drawing Sheets

Figure 1    Preparation of asoprisnil
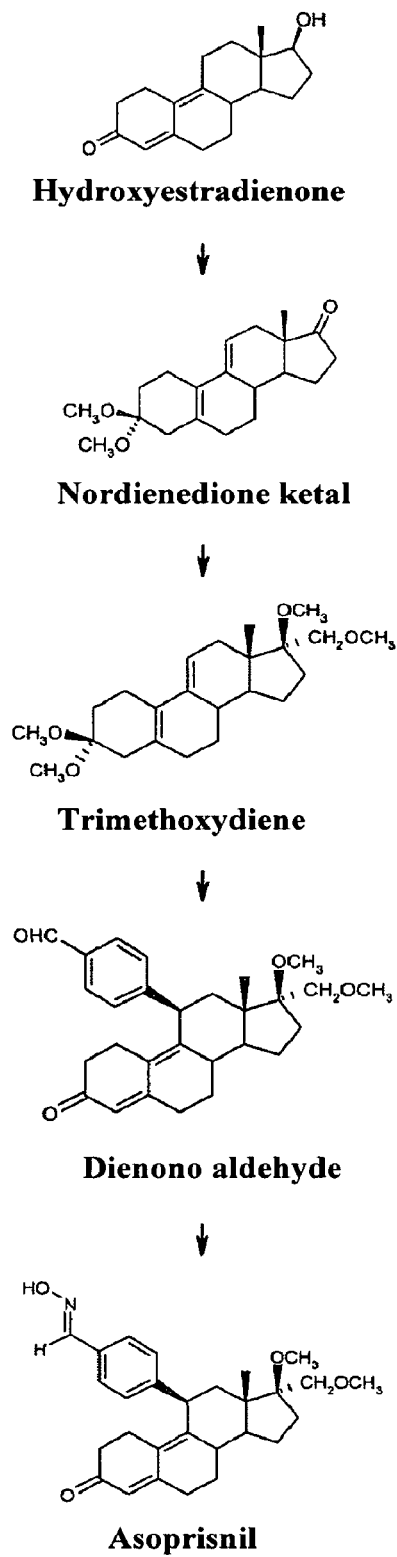

Figure 2 Synthesis of 3,3-dimethoxyestra-5(10),9(11)dien-17-one (nordienedione ketal) from 17β-hydroxyestra-4,9-dien-3-one (hydroxyestradienone)
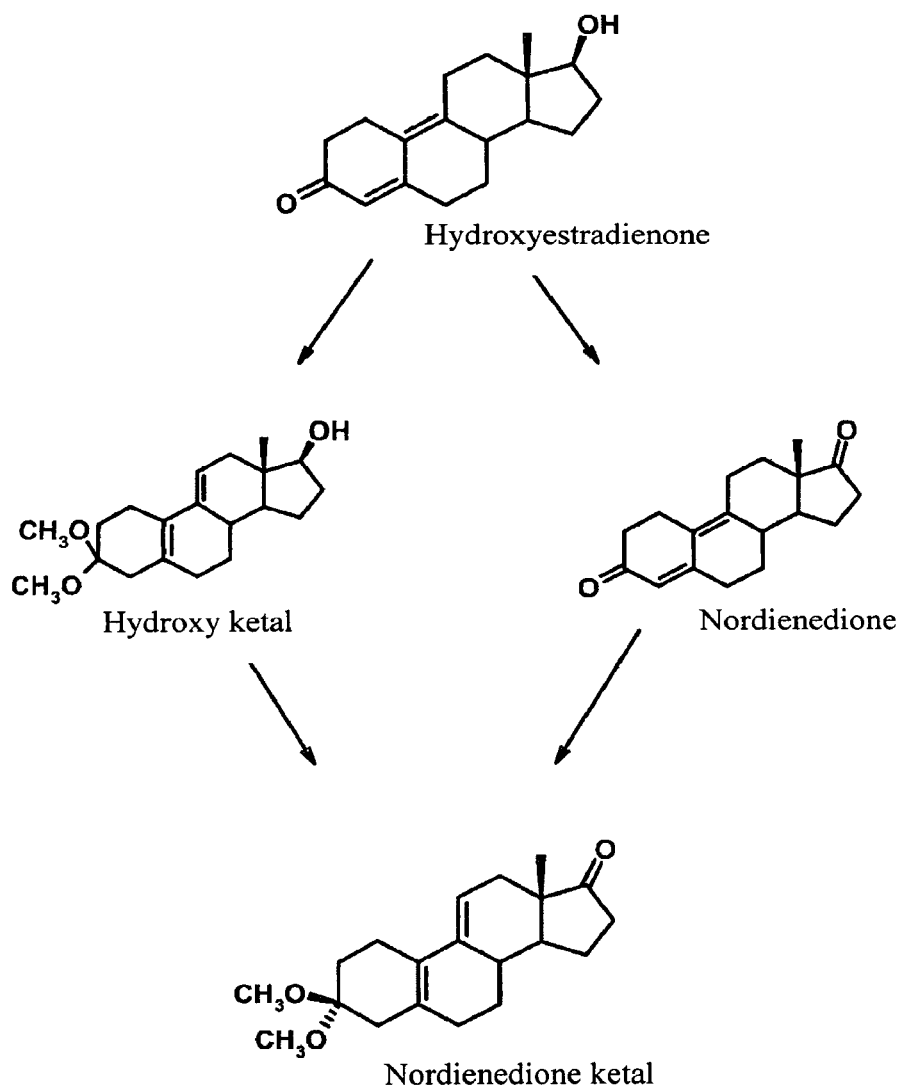

Figure 3  DSC at 5K/min
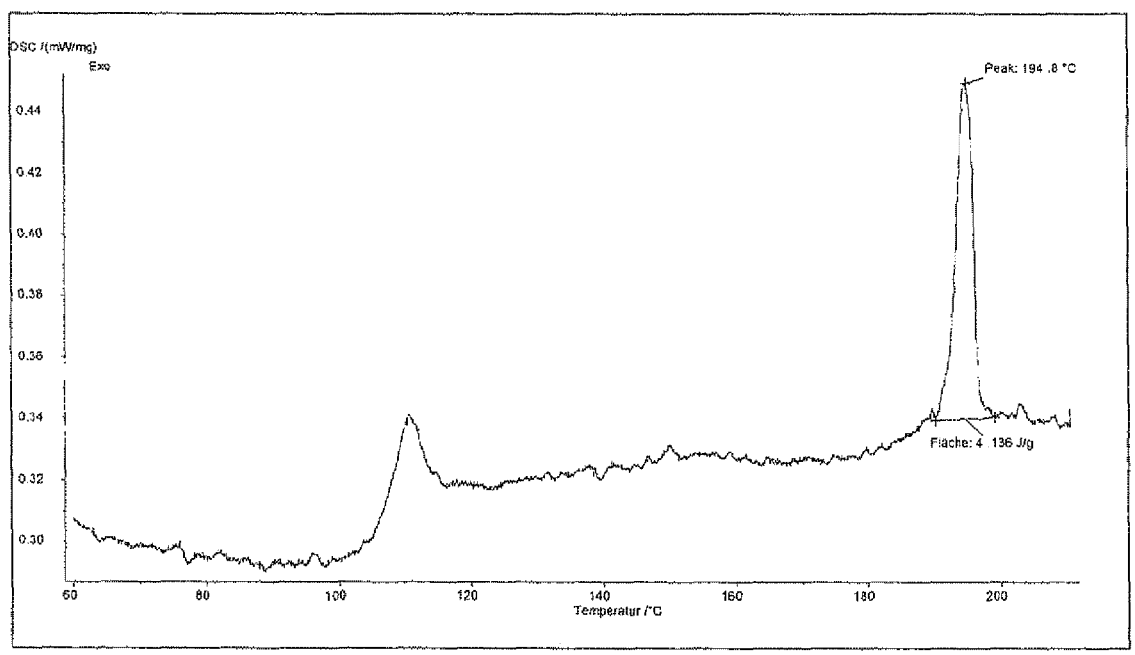

METHOD FOR PREPARING 4-[17β-METHOXY-17α-METHOXYMETHYL-3-OXOESTRA-4,9-DIEN-11β-YL]BENZALDEHYDE (E)-OXIME (ASOPRISNIL)

This application is a continuation of U.S. application Ser. No. 11/785,421, filed Apr. 17, 2007 now abandoned, which claims the benefit of the filing date of U.S. Provisional Application Ser. No. 60/792,643 filed Apr. 18, 2006, which is incorporated by reference herein.

The present invention relates to a method for the reliable and reproducible preparation of 4-[17β-methoxy-17α-methoxymethyl-3-oxoestra-4,9-dien-11β-yl]benzaldehyde (E)-oxime (asoprisnil) on the pilot and manufacturing scale. Asoprisnil, which is prepared by this method, is distinguished by a very good physical stability and is therefore particularly suitable for the manufacture of solid pharmaceutical forms (tablets, coated tablets, etc.) which even withstand ICH accelerated conditions (40° C., 75% r.h.).

The preparation of a asoprisnil on the laboratory scale is described for example in DE 43 32 283 A1; further details on asoprisnil can be found in EP 0571 15, DE 35 04 42, DE 100 56 675 A1 and DE 100 56 676 A1.

Intermediates for preparing asoprisnil, for example the preparation of 3,3-dimethoxyestra-5(10),9(11)-diene-17-one (nordienedione ketal) are described in French patent 151 4 086 and in a publication in "Pharmazie 39, No. 7 (1984)" (B. Menzenbach, M. Hübner, R. Sahm, K. Ponsold: "Synthese potentieller Metaboliten der STS 557 (Dienogest)"), the preparation of 3,3,17β-trimethoxy-17α-methoxymethyl-estra-5 (10): 9(11)-diene (trimethoxydiene) from nordienedione ketal in EP 0 648 779, EP 0 648 778, EP 0 411 733, DD 289539, DE 100 56675, and the preparation of dienone aldehyde and asoprisnil in DE 43 32 283.

EP 129 26 07 describes novel solid forms of asoprisnil, in particular a high-purity and stable amorphous or highly crystalline form (ansolvate/anhydrate), a method for the preparation, and the use in pharmaceutical compositions. The solid forms are distinguished in particular by high stability.

These preparation methods describe the principle of the preparation of the various intermediates and of the target product, the active ingredient 4-[17β-methoxy-17α-methoxymethyl-3-oxoestra-4,9-dien-11β-yl]benzaldehyde (E)-oxime (asoprisnil) on the laboratory scale. Details of reaction conditions for preparing asoprisnil on the pilot or even manufacturing scale are not disclosed in the literature.

According to the details disclosed in the literature, it is not possible to prepare the individual intermediates on the manufacturing scale in such a way that the medicinally active asoprisnil and its precursors can be obtained therefrom reliably and reproducibly and having the analytical parameters required by the authorities or by the legislation pursuant to ICH Q6A Guidance, 2000, such as byproduct profile, content of active ingredient, chemical and physical purity, and stability. Thus, although the amorphous solid form described in EP 129 26 07 shows good stability as pure active ingredient, in the solid pharmaceutical form there is partial to complete recrystallization under ICH accelerated conditions (40° C., 75% r.h.). The suitability of the asoprisnil obtainable by this method for a solid pharmaceutical form is accordingly low.

It is therefore an object of the present invention to provide a productive and reliable method for preparing asoprisnil with which the active ingredient can be prepared reproducibly in high purity and yield on the pilot and manufacturing scale. By purity is meant the physical and chemical purity of the active ingredient.

This object is achieved by the present multistage method for preparing 4-[17β-methoxy-17α-methoxymethyl-3-oxoestra-4,9-dien-11β-yl]benzaldehyde (E)-oxime, comprising the following stages (see FIG. 1):

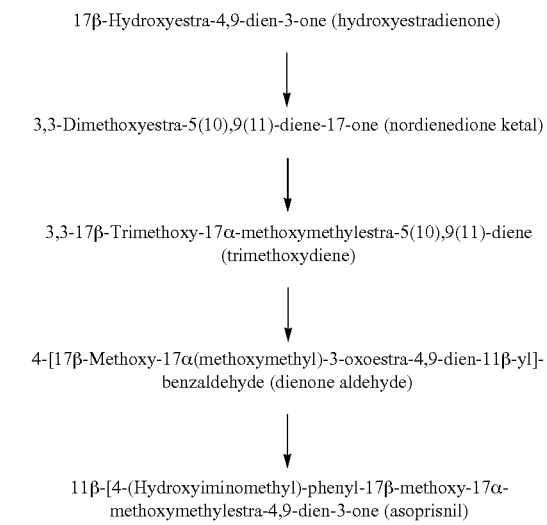

17β-Hydroxyestra-4,9-dien-3-one (hydroxyestradienone)

↓

3,3-Dimethoxyestra-5(10),9(11)-diene-17-one (nordienedione ketal)

↓

3,3-17β-Trimethoxy-17α-methoxymethylestra-5(10),9(11)-diene (trimethoxydiene)

↓

4-[17β-Methoxy-17α(methoxymethyl)-3-oxoestra-4,9-dien-11β-yl]-benzaldehyde (dienone aldehyde)

↓

11β-[4-(Hydroxyiminomethyl)-phenyl-17β-methoxy-17α-methoxymethylestra-4,9-dien-3-one (asoprisnil)

In the first stage of the method (see FIG. 2), the synthesis of 3,3-dimethoxyestra-5(10),9(11)-dien-17-one (nordienedione ketal) from 17β-hydroxyestra-4,9-dien-3-one (hydroxyestradienone), the nordienedione ketal is obtained either by oxidation of 17β-hydroxyestra-4,9-dien-3-one (hydroxyestradienone) to estra-4,9-diene-3,17-dione (nordienedione) and subsequent selective ketalization to 3,3-dimethoxyestra-5(10),9(11)-diene-17-one (nordienedione ketal) or by ketalization of hydroxyestradienone to 17β-hydroxy-3,3-dimethoxyestra-5(10),9(11)-diene (hydroxy ketal) and subsequent oxidation to nordienedione ketal.

The second stage of the method, the preparation of 3,3,17-trimethoxy-17α-methoxymethylestra-5(10),9(11)-diene (trimethoxydiene) from nordienedione ketal takes place in three steps via the stages 3,3-dimethoxyestra-5(10),9(11)-diene-17β-spiro-1',2'-oxirane (nordienespirane) and 3,3-dimethoxyestra-5(10),9(11)-dien-17β-ol (nordiene ether).

In a third stage, trimethoxydiene is converted into the corresponding 5α,10α-epoxide (enepoxide) and, in a subsequent Cu(I)-catalyzed Grignard reaction with 4-bromobenzaldehyde dimethyl ketal, converted into the so-called dimethoxy acetal (3,3,17β-trimethoxy-11β-[4-(dimethoxymethyl)phenyl]-17α-methoxy-methylestr-9-en-5α-ol). Reaction of the dimethoxy acetal with acids such as, for example, with 85 to 95% strength acetic acid affords 4-[17β-methoxy-17α-methoxymethyl-3-oxoestra-4,9-dien-11β-yl]benzaldehyde (dienone aldehyde).

The procedure reduces the formation of byproducts and thus ensures the reproducibility and validatability of each individual step in this stage of the method. The resulting product has a purity which is proved by specified individual analytical assessments (HPLC purity, UV content), and whose preparation reliably and reproducibly reduces the amounts of impurities such as, for example, byproducts of the Grignard reaction (Wurtz products), 11α-aldehyde and 5α-OH aldehyde.

For the final stage, the synthesis of 4-[17β-methoxy-17α-methoxymethyl-3-oxoestra-4,9-dien-11β-yl]benzaldehyde (E)-oxime-asoprisnil-dienone aldehyde is reacted with hydroxyamine hydrochloride in organic solvents such as, for example, pyridine or methylene chloride as described in DE 43 32 283.

The product is subsequently worked up and purified by methods known to the skilled person, such as, chromatography, fractional filtration or crystallization, and subjected to a spray drying. It is particularly important in this connection to prepare amorphous asoprisnil microparticles which have a high and, in particular, reproducible physical purity and stability in the solid pharmaceutical form. It is known that there is a high risk of recrystallization in the preparation of pure amorphous forms of active ingredients by spray drying, which recrystallization may occur in the active ingredient alone or through contact with excipients of the pharmaceutical form (Nurnberg, Acta Pharmaceutica Technologica, 26, 1980).

Both the crystalline and the amorphous form of asoprisnil described in EP129 26 07 satisfy the requirements to be met by the stability as active ingredient and for pharmaceutical processing. However, the asoprisnil microparticles must additionally show sufficient stability as active ingredient (Drug Substance) in the solid pharmaceutical form itself under ICH accelerated conditions. This makes special demands on the physical purity, which in amorphous structures has a direct effect on the stability thereof in relation to recrystallization. It is therefore indispensable for no detectable recrystallization of these microparticles to occur both during storage of the solid pharmaceutical form under normal conditions (25° C., 60% r.h.) and under accelerated conditions (40° C., 75% r.h.). The reliable and, in particular, reproducible preparation of these microparticles makes special demands on the purification and drying of asoprisnil.

The method according to the invention therefore also includes a step for drying asoprisnil in which a contamination of the microparticles with seed centres is greatly reduced through a suitable procedure.

In every spraydrying system dried particles are deposited to a greater or lesser extent on hot inner surfaces of the apparatus, e.g. on the tower wall. It has surprisingly been found that wetting events resulting from incompletely vaporized drops which are associated with an only brief and localized increase in the ethanol concentration in the particle layer cause the formation of so-called seed crystals within a few seconds. By seed crystals are meant microscopic or submicroscopic crystallites or crystalline clusters which are thermodynamically stable and are the starting point for recrystallization processes (I. Gutzow, J. Schnelzer, 'The Vitreous State', Springer Verlag 1995, Chapter 9, page 221).

In the present method according to the invention, the spray-drying process is characterized in that the largest drops in the spray cone produced by the atomizing device are vaporized so rapidly that even isolated wetting events on surfaces of the apparatus with which the product makes contact are very substantially decreased or, better, precluded. This wetting effect is reduced or even precluded to a distinctly higher degree than usual in conventional spray drying.

The size distribution of the drops generated in the atomizing unit depends on the atomizing device (pressure nozzle, rotating disc, twin fluid nozzle), the geometry thereof, and on the atomization parameters. The twin fluid nozzle generates, for example by comparison with other atomizing devices, a very fine but very broad range of drop sizes. The rotating disc by contrast a coarser but, on the other hand, narrower range of drop sizes. The particle size distribution of the dried particles is determined by the range of drop sizes.

For use of asoprisnil as drug substance for example in oral low-dose forms it is crucial to generate a particular particle size distribution. On the one hand, the uniformity of content (CUT—Content Uniformity) and, on the other hand, especially for hydrophobic substances of poor solubility like asoprisnil, the kinetics of dissolution of the active ingredient from the pharmaceutical form must be ensured. Traditionally, a technology with which the dried active ingredient is subsequently micronized is generally usual. This takes place preferably in jet mills and means an additional method step associated with high risks for the stability of solids and the purity of phases. The high energy input frequently leads to phase transformations or to the generation of seed centres for phase transformations.

It is known that amorphous substances like asoprisnil often dry from solutions to form a solid film on the surface of drops. Only subsequently and distinctly more slowly do the liquid contents of the globule vaporize from a blow-out orifice or by diffusion. The measured particle sizes are therefore insubstantially smaller than the drops from which they are formed. This second phase of drying delays the kinetics of drying of large drops even further. Whether a drop can be completely vaporized and dried to a particle during the spray drying depends not only on its size but also on the geometric and aerodynamic conditions in the drying tower, e.g. on the length of the flight path available and the velocity (Nurnberg, Acta Pharmaceutica Technologica, 26, 1980; Bauckhage, Chem. Ing. Technik 62 (1990), No. 8; Zbicinski, Chemical Engineering Journal 86, 2002, pp. 207-216).

A further advantageous configuration of the method according to the invention therefore consists of obtaining the active ingredient asoprisnil after the spray drying in the form of amorphous microparticles with a particular particle size distribution in one method step without subsequent micronization.

Particularly preferred embodiments of the method according to the invention are described below, consisting of the following stages: hydroxyestradienone→nordienedione ketal→trimethoxydiene→dienone aldehyde→asoprisnil (see FIG. 1).

The hydroxyestradienone starting material of the method according to the invention can be obtained by methods known to the skilled person (Menzenbach, Bernd; Huebner, Michael, Zeitschrift für Chemie (1986), 26(10), 371ff).

1. Nordienedione Ketal 1.1. Nordienedione Ketal Via Nordienedione (Hydroxyestradienone→Nordienedione→Nordienedione Ketal)

Chromic Acid Oxidation of Hydroxyestradienone

The carrying out of chromic acid oxidations in the synthesis of steroid active ingredients is a synthesis stage which is widely used and described in detail in the specialist literature. Steroidal alcohols are oxidized to ketones using a mixture of chromic acid and sulphuric acid (Jones' reagent, J. Chem. SOC. 1946, 39 and J. Chem. Soc. 1953, 2548). This chromic acid oxidation is carried out in various solvents such as acetone, DMF, dichloromethane and chloroform. DMF and chloroform may in many cases be replaced by the less physiologically and ecologically objectionable acetone. Disadvantages of this replacement of DMF and chloroform by acetone are the incomplete and non-reproducible conversion of the starting material. For example, unreacted hydroxyestradienone can be removed only with great difficulty and is therefore "carried over" as impurity throughout the synthesis of the active ingredient, thus greatly impairing the quality of the synthesized product.

Complete and reproducible chromic acid oxidation of hydroxyestradienone is carried out according to the invention in acetone by managing the reaction as two-phase reaction between liquid phases. To this end, a certain amount of water is added to a solution of hydroxyestradieneone in acetone in such a way that the water content of the organic phase passes through a minimum in the distribution equilibrium of the water between organic phase and the aqueous chromic acid phase. This minimum arises through the surprising occurrence of a phase change in the inorganic chromic acid phase, which extracts water from the inorganic phase despite an increase in total water content of the reaction solution. The result of this is that
1. the solubility of the organic phase for the steroid is improved,
2. the chromium sludge cannot trap any starting material because its viscosity can be instantaneously reduced and
3. thus a very large mass transfer area can be created by the agitator.

This minimum is influenced by the temperature and concentration conditions in the chromic/sulphuric acid. The optimum of these parameters can be determined experimentally by the skilled person.

The complete and, in particular, reproducible reaction is achieved by adding water, preferably 2-10% by weight based on acetone, to a solution of hydroxyestradienone in acetone in such a way that a defined systemic water concentration (added water plus water from the chromic/sulphuric acid), preferably of 10-15% by weight, is adjusted, with the steroid concentration not exceeding 8 g/l of acetone. The subsequent selective monoketalization of the diketone nordienedione is carried out according to the invention with Lewis acids according to the following variants:
1. Selective ketalization with silicon tetrachloride and methanol
    a) silicon tetrachloride is put into a mixture of methanol and n-hexane solvents, with the addition taking place in a temperature range from −5 to 15° C., preferably 2 to 10° C.;
    b) rapid addition of nordienedione is in the aforementioned temperature range from −5 to 15° C., preferably 2° C. to 10° C.;
    c) stirring during crystallization, where the solution obtained in b) is preferably stirred at 5° C. to 15° C., particularly preferably 10° C., for 60 to 100 minutes, and then at −8° C. to 0° C. to complete the crystallization;
    d) the resulting crystals are isolated using a solid/liquid separating device and are then washed alternately with methanol and hexane or methanol/aqueous ammonia
    e) drying of the resulting nordienedione ketal or
2. selective ketalization with acetyl chloride and methanol using a solution of the crude product from the chromic acid oxidation.

The described variants of a specific procedure for the selective ketalization of nordienedione are distinguished by the formation of byproducts being greatly reduced. The said methods afford a product which makes specified individual analytical assessments reliably and reproducibly possible and satisfies high quality demands.

1.2. Nordienedione Ketal Via Hydroxy Ketal

In this variant, firstly 17β-hydroxyestra-4,9-dien-3-one (hydroxyestradienone) is ketalized to give the intermediate 17β-hydroxy-3,3-dimethoxyestra-5(10),9(11)-diene (hydroxy ketal). This is followed by oxidation to a nordienedione ketal by Oppenhauer oxidation:
hydroxyestradienone→hydroxy ketal→nordienedione ketal Purification takes place by usual methods known to the skilled person, for example by chromatography or fractional filtration. Examples thereof which may be mentioned are the following solvents such as methanol, heptane, cyclohexane, methyl tert-butyl ether as well as combinations thereof, and mixtures of solvents such as, for example, methyl tert-butyl ether/heptane, cyclohexane/methyl tert-butyl ether, isopropanol/water. Cyclohexane/methyl tert-butyl ether are particularly suitable.

The support material used for a purification by chromatography is for example aluminium oxide.

The ketalization with trialkyl orthoformates in methanol is described in detail for steroid active ingredients in the specialist literature (Byer, Walter, Lehrbuch der organischen Chemie, 21$^{st}$ Edition, S. Hirzel Verlag Stuttgart, p. 216).

Steroids which have a keto function in position 3 are converted into the corresponding dimethyl ketals by using trimethyl orthoformate in mixtures of solvents containing methanol. In conventional ketalization methods, sulphuric acid or sulphuric acid derivatives such as, for example, p-toluenesulphonic acids are added as catalysts. One disadvantage of the procedure mentioned is that these catalysts must subsequently be removed by extraction. Ketals are unstable under these aqueously acidic conditions.

The ketalization is therefore carried out according to the invention on an acid-activated ion exchanger. The ion exchanger can be put directly into the reaction solution. The advantage of this is that the ion exchanger can easily be removed again by filtration. A further variant of the configuration of the ketalization consists according to the invention of passing the reaction solution over the acid-activated ion exchanger in a so-called bypass method. This means that removal of the ion exchanger is no longer necessary.

Oppenhauer oxidation of steroids is likewise described in detail in the specialist literature (Byer, Walter, Lehrbuch der organischen Chemie, 21' Edition, S. Hirzel Verlag Stuttgart, p. 216). Steroids with a 17-hydroxy function are oxidized to the corresponding 17-ketones by using aluminium alcoholates and cyclohexanone. However, it is not possible to carry out the reaction hydroxy ketal nordienedione ketal quantitatively using conventional aluminium alcoholates such as, for example, aluminium triisopropoxide. For this reason, the reaction is carried out according to the invention with aluminium diisopropoxide trifluoroacetate (DIPAT) as catalyst in the presence of cyclohexanone. The hydroxy ketal is reacted virtually completely through the use of DIPAT.

The nordienedione ketal product of the reaction results as crude product. However, it is possible with conventional methods such as, for example, recrystallization to achieve a purity of only less than 90%. For this reason, the prepared nordienedione ketal is dissolved according to the invention in methyl tertiary butyl ether, filtered through aluminium oxide and then eluted with a mixture of cyclohexane and methyl tertiary butyl ether. The product is obtained with a purity of more than 95%.

2. Trimethoxydiene Via Nordienespirane and Nordiene Ether

Nordienespirane is prepared from nordienedione ketal according to DE 100 56 675 with trimethylsulphonium iodide and potassium tertiary butoxide in DMF. Nordienespirane is then converted with sodium methanolate in methanol into nordiene ether. A precondition for its further conversion to trimethoxydiene according to the following sequence
nordienedione ketal→nordienespirane→nordiene ether→trimethoxydiene
is that the nordiene ether is isolated and purified in a complicated manner.

On further processing in solution, for conversion to be as quantitative as possible it is necessary to remove as completely as possible from the nordiene ether solution the residues of water and methanol originating from the precursors.

Virtually complete conversion to trimethoxydiene is achieved according to the invention by a) carrying out at the nordienespirane stage the reaction in DMF in an initial phase with addition of the reactants in a temperature range from 0 to 25° C., preferably between 0 to 20° C. and in an after-reaction phase between 20 to 40° C., preferably between 30 to 35° C.;
b) the reaction product obtained in step a) not being isolated but being employed as solution of nordienespirane in solvents, preferably in hexane, DMF or in THF;
c) for conversion of the nordienespirane from step b) into the nordiene ether changing the solvent, preferably during the reaction with sodium methanolate, particularly preferably by azeotropic distillation, and thus reaching the required reaction temperatures of 70° C. or more;
d) at the trimethoxydiene stage crystallizing from methanol by cooling a steroid solution, preferably a solution with 40-50% by weight steroid, to 20-35° C., preferably 25° C., for about 1 to 2 hours, and then cooling further to −5° C. to −15° C., preferably −10° C.

Since the water and solvent contents in the starting material for conversion of nordienedione ketal into nordienespirane play a substantial part, a virtually complete conversion is achieved in this stage by limiting the amounts of methanol and water, which are considerable as a result of the preparation, in the nordienedione ketal. This is ensured when the water content is less than 1%, preferably less than 0.6% and the methanol content is less than 1%, preferably less than 0.8%, in the nordienedione ketal.

Changing the solvent in the conversion of nordienespirane to nordiene ether, for example from hexane to methanol, preferably by azeotropic distillation, allows the synthesis to be continued without high-loss and complicated intermediate isolation of the nordienespirane.

Since the water and solvent contents in the starting material for conversion of nordiene ether into trimethoxydiene play an equally large part as in the abovementioned conversion of nordienedione ketal into nordienespirane, in this case too complete conversion to trimethoxydiene is guaranteed by reducing the amounts of water and methanol derived from the nordiene ether stage, preferably by azeotropic distillation, to below 0.8% water, particularly preferably below 0.4% water. Removal of unreacted nordiene ether is no longer possible later.

The specific temperature control has the effect of distinctly reducing the formation of byproducts while, at the same time, conversion is virtually complete and rapid. In particular, the formation of the 17α epimers of nordienespirane and the formation of 16-methyltrimethoxydiene are greatly minimized.

The specific management of the crystallization guarantees a very good reduction in the amount of byproducts in the crystals. In particular, unreacted nordiene ether and byproducts such as, for example, the 17-oxetane compound of the nordiene ketal remain in solution. The resulting product can very easily be filtered, washed and dried.

3. Dienone Aldehyde Via Enepoxide and Dimethoxy Acetal

Trimethoxydiene is dissolved in dichloromethane and pyridine. Hexafluoroacetone is added as catalyst for the subsequent epoxidation. A hydrogen peroxide solution is metered in at 25 to 35° C. After conversion has taken place, the phases are separated. The organic phase is, after removal of the peroxides by washing with water, sodium bicarbonate solution and sodium thiosulphate solution, changed to THF by distillation. The dimethoxy acetal is prepared by a Grignard reaction from enepoxide and magnesium in THF with bromobenzaldehyde dimethyl acetal. Bromobenzaldehyde dimethyl acetal is obtained by acetalization of 4-bromo-benzaldehyde with trimethyl orthoformate in organic solvent such as, for example, methanol and THF in the presence of an acidic catalyst, for example sulphuric acid derivatives (e.g. p-toluenesulphonic acid). For this, the reaction is carried out as described under 1.2. with an acid-activated ion exchanger, with the ketalization taking place by a bypass method according to the invention in a preferred variant of the method. As the skilled person is aware, activation of the magnesium turnings for the Grignard reaction, for example with dibromoethane or DIBAH, may be necessary in some circumstances. A catalytic amount of copper(I) chloride is added to the Grignard solution, which can be controlled before use for example to a temperature of 10 to 20° C., under inert conditions and with stirring. Subsequently, preferably within less than 60 minutes, a solution of 17α-(methoxymethyl)-3,3-17β-trimethoxy-5α,10α-epoxyestr-9(11)-ene and THF is added to the stirred Grignard solution at −10° C. to 55° C., maximally 45° C., and subsequently an after-reaction is carried out at the same maximum temperature. Working up takes place by methods known to the skilled person.

4. Asoprisnil
4.1. Synthesis

The stage for preparing asoprisnil as crude product is composed according to the invention of the following individual steps:

a) a suspension or solution of dienone aldehyde, for example in pyridine or methylene chloride, is mixed with a solution of hydroxyamine-hydrochloride in pyridine
b) the reaction solution obtained in step a) is put at a temperature of 0-30° C., preferably 20-25° C., into a solvent, preferably ethyl acetate, methylene chloride or toluene, which is controlled at a temperature of 5-15° C., with stirring, and acidified with hydrochloric acid or sulphuric acid;
c) working up takes place by
  crystallization by adding methyl tertiary butyl ether to the solution and thus obtaining a methyl tertiary butyl ether solvate with 12-20% methyl tertiary butyl ether and subsequently drying, or
  filtration, preferably through silica gel, changing to methanol by distillation, precipitation with water and drying of the solid obtained in this way.

4.2. Working Up

The working up of the asoprisnil obtained from the synthetic method described above takes place by HPLC purification and subsequent spray drying, the procedure for which is described below.

The HPLC purification can be carried out by methods known to the skilled person.

A solution of asoprisnil in alcohol, preferably in lower alcohols such as ethanol, methanol and isopropanol, is sprayed with a specific temperature regime into a spray-drying system as described in WO 01/90137. This regime is such that the outlet temperature of the drying gas is kept at 40° C. to 90° C., preferably 75° C. to 90° C. Moreover, the mass ratio of spraying gas employed to sprayed solution is 1.5 to 10, preferably from 2.5 to 5, and the mass ratio of drying gas employed to sprayed solution employed is at least 10, preferably at least 20. Moreover, the dried asoprisnil particles are separated from the drying gas on a product filter and deposited virtually completely in a collecting vessel. It has been found that the otherwise usual deposition of spray-dried particles via a cyclone surprisingly leads to distinctly more unstable products in the case of asoprisnil. The deposition of the spray-dried asoprisnil particles on a product filter is therefore a particularly advantageous embodiment of the invention. The use of fresh, unused filter surfaces for each production run is a further advantageous configuration of the invention, since a product with the desired stability properties is prepared in this way. Even a few ppm of crystalline asoprisnil particles lead to a significant destabilization of the amorphous product. It has emerged that despite thorough purification with the usual solvents such as ethanol or methanol surprisingly small residues of crystalline substances remain in the material on the filter which contaminate the amorphous product with crystal seeds. The spray drying is followed by an after-drying. In this procedure, the microparticles are treated under vacuum of <100 mbar, preferably less than 10 mbar, and at a temperature of less than 90° C., preferably less than 50° C., and/or with flushing with a solvent-free drying gas for a lengthy period until the alcohol content is less than 1%, preferably less than 0.5%, in order to stabilize the amorphous structure further.

The described procedure results in physically pure and stable amorphous asoprisnil microparticles The term "physical purity" refers here, in accordance with the literature (A. Burger, Pharmazie in unserer Zeit 26, 1997, 93), to a chemically pure substance which essentially comprises impurities of the same chemical substance but in a different solid state (polymorphous, amorphous, pseudopolymorphous) only in small amounts. Depending on the type of substance, these physical impurities can be measured quantitatively by thermomicroscopy, differential scanning calorimetry (DSC), x-ray powder diffractometry or other methods.

The present invention accordingly relates to a method for the reliable and reproducible preparation, working up and purification of amorphous asoprisnil, which can be carried out on the manufacturing scale. The method according to the invention makes it possible to prepare asoprisnil on the pilot and/or manufacturing scale in high purity with an overall yield of crude, i.e. not yet purified, asoprisnil of 58% (gross). Taking account of the active ingredient content in the asoprisnil final product, a yield of 47% (net) is achieved.

Methods previously disclosed for preparing asoprisnil on the laboratory scale, as published in DE 433 2283, WO 02/38582 and WO 02/38581, disclose yields of between 5 and 23%. Comparison of the yields achieved is possible only with provisos because the syntheses start from different starting materials and/or take place by different routes. Compared with the methods described in DE 433 2283 and WO 02/38582, which start at a substantially later point, namely 3,3-dimethoxy-5α,10α-epoxyestr-9(11)-en-17-one, and compared with the method described in WO 02/38581, which starts from a likewise later starting material—3,3-dimethoxyestra-5(10),9(11)-dien-17-one—, the method according to the invention, starting from 17β-hydroxyestra-4,9-dien-3-one (hydroxyestradienone) via the following stages

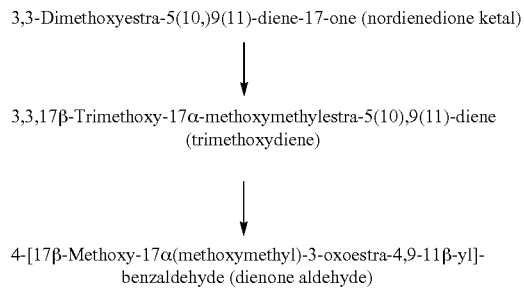

11β-[4-(Hydroxyiminomethyl)-phenyl-17β-methoxy-17α-methoxymethylestra-4,9-dien-3-one (asoprisnil) achieves a distinct increase in the yield to 47 or 58%. The method according to the invention surprisingly achieves an improvement in the yield despite conversion of far larger quantities, i.e. on the pilot or manufacturing scale, than described in the laboratory methods previously published. A further advantage of the method according to the invention is that each individual stage of the method can be carried out reliably and reproducibly on the pilot and manufacturing scale.

The method according to the invention for preparing asoprisnil can be carried out in accordance with the following examples, these serving for detailed explanation without restricting the invention.

The method can be carried out by employing the agitated reactors, distilling apparatuses, crystallizers, centrifuges and dryers customary in batch-oriented chemical practice.

1. Nordienedione ketal 1.1. Nordienedione ketal via nordienedione

Variant A 12 kg of hydroxyestradienone are dissolved in 180 l of acetone and then 7.5 l of water are added. Chromic/sulphuric acid for oxidation is prepared from 50 l of water, 18 kg of chromium trioxide and 12 l of sulphuric acid. At 15° C., 17.5 l of this chromic/sulphuric acid with 260-270 mg of chromium trioxide/ml are added over the course of one hour and then reaction is continued at 22-25° C. for 1 hour. Working up takes place by the usual methods known to the skilled person ($Cr^{6+}$ reduction with bisulphite, concentration and crystallization from acetone/water mixtures).

33 l of methanol and 46 l of n-hexane are controlled at a temperature of 2-10° C. To them are added firstly 1.2 kg of $SiCl_4$ and then 10 kg of nordienedione with stirring. After crystallization starts, the mixture is stirred at 5-15° C. for 1 hour to 1.5 hours and then cooled to 0 to −8° C. and filtered with suction. If crystallization does not start unaided, seeding is also possible in a conventional way. The crystals are washed on a fit with hexane and ammoniacal methanol. Drying results in 80-109% of expected. The qualities which can reliably be achieved are set forth in the specification and are achieved with the method according to the invention, including purity 95 A % (HPLC), proportion of unreacted nordienedione=0.2 A %, largest unspecified byproduct=1.0 A %.

Variant B 100 g of hydroxyestradienone are introduced into 400 ml of acetone and 20 ml of water. A chromic/sulphuric acid solution prepared from 101 ml of water, 35.6 g of chromium trioxide and 32 ml of sulphuric acid is metered in at an internal temperature of 12° C. in such a way that ¾ is metered in in two hours and the remainder in a further 2 hours. After stirring for 30 minutes, excess chromic acid is decomposed by adding 26 ml of isopropanol. The change to water is then effected by distillation in vacuo at an internal temperature of 60° C. About 400 ml of water are required for this. The precipitated intermediate (nordienedione) is filtered off with suction and washed with water until neutral.

Nordienedione is then dissolved in 170 ml of methylene chloride and stirred with 3.6 g of kieselguhr for 20 minutes. Kieselguhr is filtered off and the filtrate is washed 2× with 50 ml of water each time to remove chromium salts. The organic phase is changed to methanol by distillation in vacuo and concentrated to 300 ml. 440 ml of hexane are added at an internal temperature of 20° C. The suspension is cooled to 5° C. Over the course of one minute, 26 ml of acetyl chloride are added and then washed with 37 ml of methanol. The starting material dissolves, and the product then precipitates. If necessary, seeding with nordienedione ketal takes place after 3 minutes.

After crystallization has started, the mixture is stirred for 80 minutes, then controlled to 5° C. and made alkaline by adding 37 ml of 50% strength sodium hydroxide solution. The product (nordienedione ketal) is isolated and washed firstly with a mixture of 320 ml of methanol and 13 ml of aqueous ammonia and then with 35 ml of hexane. It is sucked dry under a nitrogen atmosphere and dried in vacuo. Yield: 82.4 g of nordienedione ketal.

1.2. Nordienedione Ketal Via Hydroxy Ketal 66.7 kg of hydroxyestradienone are dissolved in 500 l of toluene and 400 ml of methanol. Filtration through 3.4 kg of activated carbon is carried out where appropriate. Addition of 51 l of trimethyl orthoformate and a further 70 l of methanol is followed by circulation by pump over 33.4 kg of activated ion exchanger at 30° C. until conversion to hydroxy ketal is complete. Addition of 20 l of pyridine and 400 l of a sodium carbonate solution is followed by stirring and separation of the phases. The aqueous phase is back-extracted several times with 135 l of toluene. The combined organic phases are concentrated to 300 l and changed to 300 l of toluene by distillation.

40 kg of aluminium isopropoxide and 180 l of heptane are introduced into a second reaction vessel. 14.7 l of trifluoroacetic acid are metered in at a temperature of 50° C. Addition of 6.7 l of pyridine is followed by removal of heptane by distillation down to 95 l. After cooling to 25° C., the organic hydroxy ketal solution is added while stirring. Addition of a total of 76 l of cyclohexanone, metered in part, is followed by stirring for up to 6 hours until conversion is complete. Addition of 570 l of a sodium hydroxide solution is followed by stirring and separation of the phases. The aqueous phase is back-extracted several times with 70 l of toluene. The combined organic phases are washed several times with 70 l of water. The mixture is concentrated to 270 l and changed to water by distillation. This results in 270 l of a suspension of crude product and water. The crude product is isolated and dissolved in 270 l of methyl tert-butyl ether. The solution is washed with 70 l of water. The aqueous phase is back-extracted with 70 l of methyl tert-butyl ether. The combined organic phases are filtered and concentrated to 135 l. After addition of 540 l of cyclohexane, the solution is filtered through 134 kg of aluminium oxide. The aluminium oxide is washed with a mixture of a total of 270 l of cyclohexane and 100 l of methyl tert-butyl ether. The product-containing fractions are concentrated and changed to 200 l of heptane by distillation. The heptane solution is cooled to −15° C., whereupon the product crystallizes. The product is isolated and washed with 35 l of heptane and 35 l of water. The nordienedione ketal product is dried at max. 40° C. until the loss on drying is ≦0.5%.

2. Trimethoxydiene Via Nordienespirane and Nordiene Ether 65.6 kg of nordienedione ketal and 50 kg of trimethylsulphonium iodide are suspended in 150 l of dimethylformamide (DMF) and cooled to 15° C. A solution of 30 kg of potassium tert-butoxide in 65 l of DMF is metered in at 20° C. The mixture is stirred at 30° C. for 30 minutes and the conversion is checked by TLC. 200 l of water and 410 l of hexane are added at 30 to 40° C. to transfer the reaction product into the hexane phase. The aqueous DMF phase is back-extracted four times with 50 l of hexane each time. The combined organic phase is washed twice with 85 l of water. The aqueous phase is back-extracted with 50 l of hexane. Subsequently concentrated in vacuo to a volume of 150 l and mixed with 130 l of methanol. About 250 l of sodium methanolate solution (30%) are added to the methanolic solution, and distillate is taken off under atmospheric pressure until at least 70° C. is reached. The mixture is then heated under reflux for 1.5 hours until the conversion is complete. Distillation is continued in vacuo with continuous addition of 215 l of water. The nordiene ether obtained in this way is taken up in 330 l of methyl tertiary butyl ether (MtBE), the organic phase is separated off and the aqueous phase is extracted twice with 100 l of methyl tertiary butyl ether each time. The combined organic phases were extracted twice with 100 l of water. The aqueous phases were back-extracted with 60 l of MtBE. This is followed by concentration in vacuo and, at a volume of 165 l, water and methanol are removed azeotropically from the organic phase with the addition of 165 l of methyl tertiary butyl ether to maintain this volume. 27.2 l of methyl iodide and 10 l of MtBE are added thereto. Then 70.5 kg of potassium tertiary butyl ether in 300 l of MtBE are metered in at 35° C. Reaction is continued for 1 to 2 hours, and the conversion is checked. After addition of 245 l of water, the organic phase is separated off and washed with 65 l of water. The aqueous phase is back-extracted with 65 l of MtBE. This is followed by concentration to about 80 l in vacuo. Distillation to change to methanol and concentration to a volume of 140 l are followed by stirring at 25° C. for 1 to 2 hours. The mixture is then cooled to below −10° C. and stirred for a further 2 hours. The product is subsequently isolated and washed with 15 l of cold methanol. Trimethoxydiene is dried in vacuo at 40° C.

3. Dienone aldehyde via enepoxide and dimethoxy acetal 3.1. Enepoxide 10.6 l of hexafluoroacetone are added to a solution of 80.6 kg of trimethoxy diene, 755 l of methylene chloride and 11 l of pyridine. 81 l of a 35% strength hydrogen peroxide solution are gradually added to this solution while stirring at a temperature of 30 to 40° C. After the addition, the mixture is stirred at 30 to 40° C. for 30 min and then a check of conversion is carried out. The organic phase is separated off and washed twice with 175 l of aqueous sodium bicarbonate solution. The organic phase is subsequently washed with 250 l of sodium thiosulphate solution. Finally, the organic phase is washed three to four times with 160 l of water. The organic phase washed in this way is concentrated in vacuo and at a temperature of 30° C. and changed to THF by distillation so that the final volume is 170 l.

3.2. Dimethoxy Acetal

The Grignard reagent is prepared from 13 kg of magnesium turnings, 280 l of THF, 7.3 kg of DIBAH and 106 l of bromobenzaldehyde dimethyl acetal. Bromobenzaldehyde dimethyl acetal is prepared by acetalization of 4-bromo-benzaldehyde with trimethyl orthoformate in methanol in the presence of acidic catalysts, preferably acidic ion exchanger, preferably in a bypass method. After addition of about 0.5 kg of copper(I) chloride, the enepoxide solution is added, the mixture is stirred at 40° C. until conversion is complete. Excess Grignard reagent is destroyed by metering in 490 l of ammonium chloride solution at max. 10° C. After addition of 142 l of dilute acetic acid, the organic phase is washed 3 to 4 times with 122 l of ammonium chloride solution. The aqueous phases are back-extracted three to four times with 90 l of ethyl acetate. The combined organic phases are washed with 170 l of sodium chloride solution and concentrated to 220 l in vacuo at 40° C.

3.3. Dienone Aldehyde

The dimethoxy acetal solution is mixed with 312 l of conc. acetic acid and 35 l of water and heated at 90° C. for about 30 min. After cooling, 680 l of water are metered in. The crude product is isolated and stirred and washed several times with 170 l, 170 l and 110 l and 340 l of MtB ether at temperatures up to 50° C. Dienone aldehyde is dried in vacuo at 30° C. to 40° C.

4. Asoprisnil 4.1. Synthesis

Variant A 15 kg of dienone aldehyde are suspended in 38 l of pyridine. To this are added 42 l of a prepared hydroxyamine hydrochloride/pyridine solution. After a successful check of conversion and taking up in 88 l of ethyl acetate, 6N HCl is added while monitoring the pH (2-4). After phase separation and extraction of the organic phase with water, the organic ethyl acetate phase is concentrated, distilled with toluene and subsequently mixed with 50 l of methyl tertiary butyl ether. Crystallization results in the target product. It is then dried.

The following purities were achieved with the method according to the invention after HPLC examination:

Oxime=92.9 area %
Aldehyde=0.08 area %
Z-Oxime=3.1 A %
Dioxime=3.1 A %

Variant B 50 kg of dienone aldehyde are dissolved in 250 l of methylene chloride. A solution of 8.86 kg of hydroxyamine hydrochloride in 130 l of pyridine is added at 20° C. over the course of 1 to 2 h. After a successful check of conversion, about 280 l of sulphuric acid are metered in at <10° C. At 10° C., the phases are separated and the aqueous phase is back-extracted twice with 120 l of methylene chloride. The organic phase is washed three times with 200 l of water, which are back-extracted with 110 l of methylene chloride. The organic phase is concentrated to 200 l in vacuo and filtered through silica gel. The organic phase is washed with about 100 l of a sodium bicarbonate solution. Distillation is carried out in vacuo to change to a final volume of 200 l of methanol. The methanolic product solution is added to 510 l of water, whereupon the crude product precipitates. Asoprisnil (crude) is isolated and dried in vacuo at 30 to 40° C.

The crude product is purified by preparative high performance liquid chromatography (HPLC). For this purpose, the asoprisnil (crude) is dissolved in dichloromethane and applied to silica gel. The substance is then eluted with a toluene/acetone mixture. A mixed fraction is obtained in addition to the pure fraction and can be rechromatographed to increase the yield. The pure fraction is concentrated and isolated in the next process step.

4.2. Working Up and Purification

EXAMPLE 1

5.1 kg of asoprisnil are dissolved in 57 l of ethanol (DAB) by heating to 60° C. The clear solution is pumped with minimal pulsation by a metering pump at 6 l/h to the twin-fluid nozzle (d=0.8 mm) of a spray dryer, cylinder d=800×620 mm, base cone 60°, co-current operation of heating and spraying gas. The asoprisnil solution is maintained at a temperature of 65° C. during this. The atomizing gas is adjusted at the nozzle to 12 Nm$^3$ N$_2$/h. The heating gas throughput is 85 m$^3$/h. The heating gas inlet temperature is adjusted so that the outlet temperature at the dryer is 78° C. to 85° C. The dried microparticles are deposited on fresh textile filters with PTFE membrane of 1 m$^2$. For this purpose, the surface of the filter is periodically pulsed free with counter-current nitrogen. After the spray-drying process, the asoprisnil powder is subjected to an after-drying process. For this purpose, the drying chamber is alternately subjected to a vacuum of 5 mbar and flushing nitrogen heated to 45° C. The vacuum and flushing phases each last 45 min. The drying time is 12 h, and the final product temperature reached is 35° C. The asoprisnil microparticles obtained in this way are analyzed and show the following characteristics:

Residual solvent content: 0.36% ethanol
Particle distribution: $d_{50}$=2.1 μm, $d_{100}$=21 μm
Enthalpy of fusion (DSC at 5K/min) 4.1 J/g (see FIG. 3)
Number of crystallites at 170° C. 1187 crystallites per mg
XRPD amorphous, no crystalline reflections

EXAMPLE 2

25 mg film-coated tablets in PVC-Al blister packs with pharmaceutically customary excipients and with 16% active ingredient according to example 1, which shows by DSC with a heating rate of 5 K/min an enthalpy of fusion of 4.1 J/g and by thermomicroscopy a crystallite number of 1187 per mg, are stored at 40° C., 75% r.h. as specified in the ICH guideline. Stability analysis with XRPD
After 9 months at 40° C., 75% r.h.: amorphous

BRIEF DESCRIPTION OF DRAWINGS

FIGS. 1 and 2 show synthesis of the invention, and
FIG. 3 shows a DSC curve for a product.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding U.S. Provisional Application Ser. No. 60/792,643, filed Apr. 18, 2006, is incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A method for preparing asoprisnil on a pilot or manufacturing scale, by reacting as follows 17β-Hydroxyestra-4,9-dien-3-one (hydroxyestradienone)
↓
3,3-Dimethoxyestra-5(10),9(11)-diene-17-one (nordienedione ketal)
↓
3,3,17β-Trimethoxy-17α-methoxymethylestra-5(10),9(11)-diene (trimethoxydiene)
↓
4-[17β-Methoxy-17α(methoxymethyl)-3-oxoestra-4,9-dien-11β-yl]-benzaldehyde (dienone aldehyde)
↓
11β- [4-(Hydroxyiminomethyl)-phenyl-17β-methoxy-17α-methoxymethyl-estra4,9-dien-3-one (asoprisnil)
comprising:
a) synthesizing nordienedione ketal from hydroxyestradienone either by oxidation of 17β-hydroxyestra-4,9-dien-3-one (hydroxyestradienone) to estra-4,9-diene-3,17-dione (nordienedione) and subsequent selective ketalization to 3,3 dimethoxyestra-5(10),9(11)-diene-17-one (nordienedione ketal) or by ketalization of hydroxyestradienone to 17β-hydroxy-3,3-dimethoxyestra-5(10),9(11)-diene (hydroxy ketal) and subsequent oxidation to nordienedione ketal, b) synthesizing trimethoxydiene from nordienedione ketal in three steps via the stages 3,3-dimethoxyestra-5(10),9(11)-diene-17β-spiro-1',2'-oxirane (nordienespirane) and 3,3-dimethoxy-17α-methoxymethylestra-5(10),9(11)-dien-17β-ol (nordiene ether), not isolating nordienespirane and nordiene ether, c) synthesizing 3,3,17β-trimethoxy-11β-[4-(dimethoxymethyl)phenyl]-17α-methoxymethyl-estr-9-en-5α-ol (dimethoxy acetal) from trimethoxydiene via 17α-(methoxymethy)-3,3,17β-trimethoxy-5α,10α-epoxyestr-9(11)-ene (enepoxide) in a Cu(I)-catalyzed Grignard reaction with bromobenzaldehyde dimethyl acetal d) synthesizing dienone aldehyde by reaction with acids e) synthesizing asoprisnil from dienone aldehyde with a hydroxyamine hydrochloride solution, f) purification by chromatography, g) drying.

2. The method according to claim 1, where hydroxyestradienone is converted into nordienedione ketal by ketalization with Lewis acids and by chromic acid oxidation or Oppenauer oxidation.

3. The method according to claim 2, where either the hydroxyestradienone is first oxidized and then ketalized.

4. The method according to claim 2, carrying out the ketalization first and an Oppenauer oxidation subsequently.

5. The method according to claim 3, where the chromic acid oxidation is carried out as two-phase reaction between two liquid phases.

6. The method according to claim 5, where water is added to a solution of hydroxyestradienone in acetone in such a way that a defined systemic water concentration is set up, with the steroid concentration not exceeding 8 g/l of acetone.

7. The method according to claim 4, where the ketalization is carried out first.

8. The method according to claim 5, where water, 2-10% by weight based on acetone, is added to a solution of hydroxyestradienone in acetone in such a way that a defined systemic water concentration of 10-15% by weight, is set up, with the steroid concentration not exceeding 8 g/l of acetone.

9. The method according to claim 4, where the ketalization is carried out first on an acidic ion exchanger.

10. The method according to claim 7, where the ketalization takes place in a bypass method.

11. The method according to claim 3, where the Oppenauer oxidation takes place with catalysis by aluminium diisopropoxide trifluoroacetate (DIPAT).

12. The method according to claim 1, where nordienedione ketal is converted completely to trimethoxydiene via nordienespirane and nordiene ether in three steps, comprising a) producing nordienespirane in DMF in an initial phase with addition of the reactants in a temperature range from 0 to 25° C., and in an after-reaction phase between 20 to 40° C.;

b) the reaction product obtained in step a) not being isolated but being employed as solution of nordienespirane in solvents;

c) conversion of the nordienespirane from step b) into the nordiene ether changing the solvent, optionally during the reaction with sodium methanolate, or by azeotropic distillation, and thus reaching the required reaction temperatures of 70° C. or more;

d) crystallizing trimethoxydiene from methanol by cooling the steroid solution, to 20-35° C., for about 1 to 2 hours, and then cooling further to −5° C. to −15° C.

13. The method according to claim 1, where the drying in g) takes place in such a way that contamination of the dried asoprisnil microparticles with seed centers in the drying device is greatly reduced.

14. The method according to claim 13, where the drying takes place by spray drying, a narrow particle size range is achieved through geometrical and aerodynamic conditions in the atomizing device, and wetting events by spray drops on surfaces of the apparatus with which the product makes contact are avoided.

15. The method according to claim 14, in which the narrow size range is generated by a high atomizing efficiency of the spraying unit by maintaining a mass ratio of spraying gas employed to sprayed solution of from 1.5 to 10, and a mass ratio of drying gas employed to sprayed solution employed of at least 10, and with a drying temperature of from 40° C. to 90° C.

16. The method according to claim 15, where the high atomizing efficiency of the spraying unit is produced by a high speed of rotation of a rotating disc or by a high atomizing gas throughput through a twin-fluid nozzle.

17. The method according to claim 13 such that the wherein spray-dried asoprisnil microparticles are subjected to an after-drying procedure which takes place in vacuo and/or with flushing of the asoprisnil microparticles with a solvent-free drying gas below 90° C., for at least 12 h.

18. The method according to claim 13, where the deposition of the asoprisnil microparticles after the spray drying takes place on a product filter, optionally using fresh unused filter surfaces.

* * * * *

UNITED STATES PATENT AND TRADEMARK OFFICE
CERTIFICATE OF CORRECTION

PATENT NO. : 8,324,412 B2  
APPLICATION NO. : 12/987850  
DATED : December 4, 2012  
INVENTOR(S) : Grawe et al.

Page 1 of 1

It is certified that error appears in the above-identified patent and that said Letters Patent is hereby corrected as shown below:

In the Claims:

Column 16, line 43 reads "17. The method according to claim 13 such that the wherein" should read -- 17. The method according to claim 13 wherein --

Signed and Sealed this
Fourteenth Day of May, 2013

Teresa Stanek Rea
*Acting Director of the United States Patent and Trademark Office*